United States Patent [19]

Shaknovich

[11] Patent Number: 5,193,546
[45] Date of Patent: Mar. 16, 1993

[54] CORONARY INTRAVASCULAR ULTRASOUND IMAGING METHOD AND APPARATUS

[76] Inventor: Alexander Shaknovich, 510 E. 85th St., New York, N.Y. 10028

[21] Appl. No.: 700,625

[22] Filed: May 15, 1991

[51] Int. Cl.$^5$ .............................................. A61B 8/12
[52] U.S. Cl. ................................................ 128/662.06
[58] Field of Search ................... 128/661.07–661.10, 128/660.10, 662.06

[56] References Cited

U.S. PATENT DOCUMENTS

| | | | |
|---|---|---|---|
| 4,637,401 | 1/1987 | Johnston | 128/662.06 |
| 4,794,931 | 1/1989 | Yock | 128/662.06 |
| 4,951,677 | 8/1990 | Crowley et al. | 128/662.06 |
| 5,000,185 | 3/1991 | Yock et al. | 128/662.03 |
| 5,002,059 | 3/1991 | Crowley et al. | 128/662.06 |
| 5,010,886 | 4/1991 | Passafaro et al. | 128/660.03 |
| 5,022,399 | 6/1991 | Biegeleisen | 128/662.06 |
| 5,069,679 | 12/1991 | Toheri | 128/662.06 X |

OTHER PUBLICATIONS

Bom, N. et al "Early and Recent Intraluminal Ultrasound Devices", Int. Jrnl. of Cardiac Imaging, vol. 4: 79–88 1989.
Bom, N. "Disposable Intra-luminal UTS Instrument", Europ. Patent PCT Publn No: 0423895A1 published Apr. 24, 1991.

Primary Examiner—Francis Jaworski
Attorney, Agent, or Firm—Brumbaugh, Graves, Donohue & Raymond

[57] ABSTRACT

An image catheter is introduced into the venous system and is maneuvered through the venous system to points adjacent to sections of arteries to be imaged. The arterial segments are then imaged from those adjacent points in the venous system. Ideally an ultrasound imaging catheter with a diameter of 7–10 French (2.3 mm–3.3. mm) operating at a frequency between 15 and 20 MHz is used.

9 Claims, 1 Drawing Sheet

CORONARY INTRAVASCULAR ULTRASOUND IMAGING METHOD AND APPARATUS

BACKGROUND OF THE INVENTION

This invention relates to methods and apparatuses for imaging arterial structures and more particularly for ultrasonically imaging epicardial arterial structures.

A conventional way of obtaining ultrasonic images indicating the condition of blood vessels, particularly arteries in the vicinity of the heart, involves insertion of an ultrasound imaging catheter directly into the artery of interest. This type of catheter, referred to as an intraarterial catheter, typically is inserted into the femoral artery and is then guided, such as with the aid of fluoroscopy, to the artery to be imaged. When in place, the catheter is activated to generate a scanning ultrasound signal which is reflected from the inner wall of the surrounding artery. The reflection signal is received by a suitable transducer and an image indicative of the cross-section of the artery is developed with the aid of electronic circuitry.

There are a number of drawbacks to this method. Since the catheter must pass through the artery, it can only image arterial sections whose interior diameters are sufficient to enable the catheter to pass through. Often arterial diseases produce blockages which can narrow an artery to the extent that the area with the blockage is too narrow for the catheter to enter. Thus the section of an artery of most interest to a physician frequently cannot be imaged with an intraarterial catheter.

Another disadvantage associated with the use of intraarterial catheters is that they can cause serious complications in patients. The introduction of a catheter into the relatively high-pressure arterial system presents a serious risk of arterial injuries such as arterial perforation, arterial thrombosis, myocardial ischemia and infarction. Due to these dangers, physicians are often reluctant to utilize intraarterial ultrasound imaging. This further impairs the usefulness of the technique.

It is the object of this invention to provide methods and apparatuses for developing images of arteries which do not suffer from the aforementioned disadvantages of the prior art.

SUMMARY OF THE INVENTION

The foregoing disadvantages of presently known intraarterial investigative techniques are overcome by the methods and apparatuses of the present invention which uses the venous system to provide access for an ultrasonic catheter to positions adjacent arteries to be imaged. The venous system is the vascular system which returns used blood to the heart. The arterial system carries fresh blood pumped by the heart to the various regions of the body and is a much higher pressure system then the venous system, especially in the vicinity of the heart. Moreover, the vessels in the venous system are often greater in cross-sectional size than their arterial counterparts and do not suffer from the disease processes which cause blockages in the arterial system.

The present invention takes advantage of the above described characteristics of the venous system, coupled with the fact that many arteries and arterial structures of interest, especially in the region of the heart, are closely adjacent to various venous structures.

In accordance with the present invention, an ultrasound catheter is inserted into the venous system and maneuvered to a venous structure, e.g. a vein, which is closely adjacent to an artery whose condition is to be investigated. The artery is then scanned by the ultrasound catheter from the adjacent vein and an image of the artery is produced by the associated electronic circuitry. Since the image is developed from outside the artery, i.e. periarterially, this technique is safer than the prior art method since the catheter never has to enter the more easily damaged, high-pressure arterial system. Furthermore, since venous structures are wider and less prone to blockage than their arterial counterparts, larger catheters can be used, thereby permitting more ultrasonic power to be used and enabling better images to be obtained. Finally, and of significant importance medically, the present method enables full imaging of a blocked artery to determine the total extent of the blockage, whereas imaging by intraarterial methods is limited to the point where a blockage prevents further movement of the catheter.

BRIEF DESCRIPTION OF THE DRAWINGS

These and other features and advantages of the invention will become more apparent from the following detailed description thereof, when taken in conjunction with the appended drawings, in which.

DETAILED DESCRIPTION OF A PREFERRED EMBODIMENT

Figure 1:
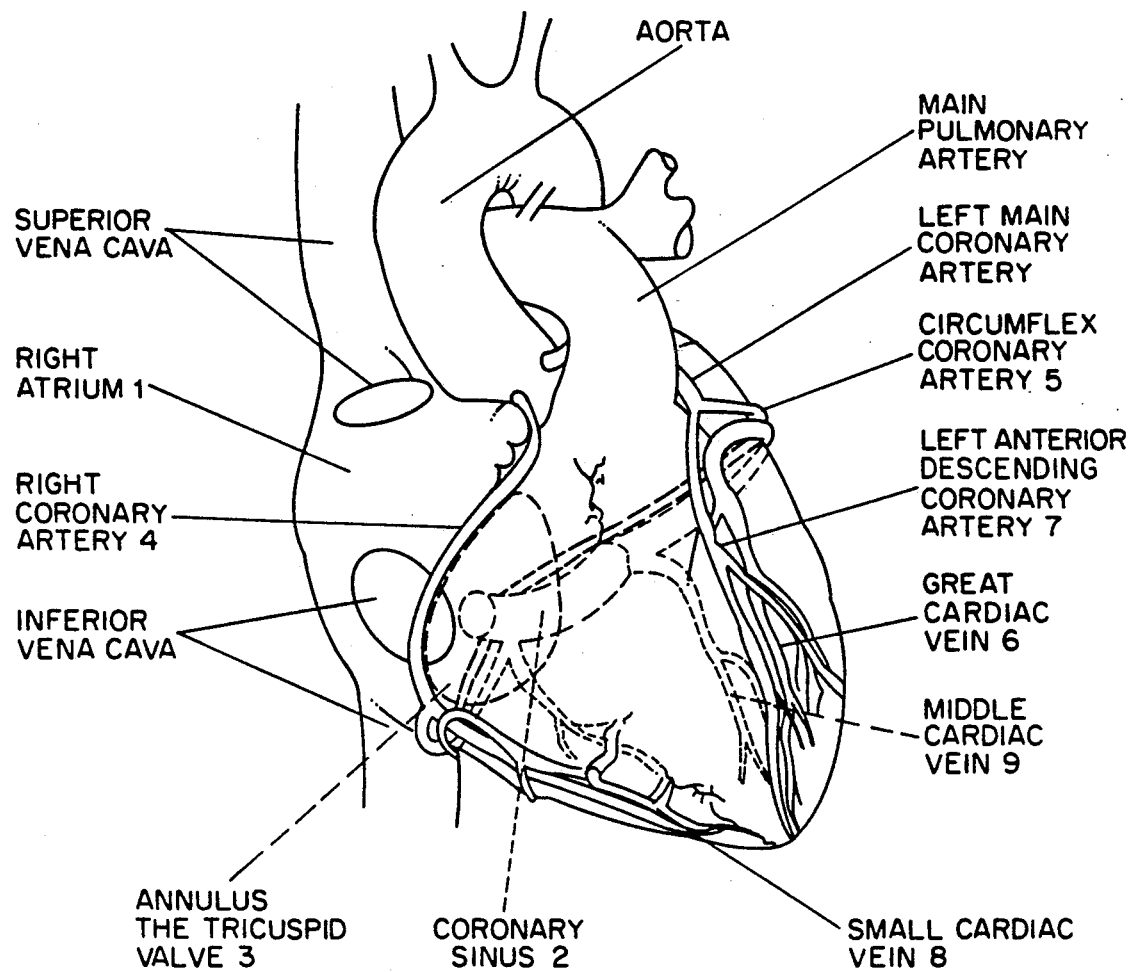
FIG. 1 is a representation of the human heart showing the coronary arteries in relation to the right atrium, the coronary sinus and the cardiac veins.

In known intraarterial ultrasound imaging procedures, an imaging catheter is inserted directly into a coronary or peripheral artery to be imaged. Usually an angioplasty guide wire is used to insert the catheter.

The imaging catheter generates a signal representative of the cross-section of the portion of the artery surrounding the imaging section of the catheter. Thus only sections of the artery wide enough to accommodate the imaging catheter can be imaged.

The imaging catheter contains a transducer which transmits a beam of ultrasound energy and receives its reflection. This reflection signal is then transmitted to processing and display devices. In order to develop an image of the entire cross-section of an artery the beam must be rotated through 360 degrees. This rotation can be achieved either mechanically or electronically.

Typically transducers in intraarterial ultrasound systems operate at 20-40 MHz. Conventional transthoracic echocardiographic devices, by contrast, operate at under 7.5 MHz. The higher frequency of the intraarterial imaging devices produces higher resolution but less penetration. Thus intraarterial ultrasound devices have an imaging depth of only a few millimeters.

Intracoronary intraarterial ultrasound catheters currently undergoing clinical trials are approximately 5 French (1.6 mm) in diameter. Thus only non-distal coronary segments greater than 1.6 mm in diameter throughout their length can be imaged. Stenoses with a residual lumen less than the diameter of the intraarterial ultrasound catheter cannot be imaged nor can portions of an artery beyond such a stenosis. This limits the usefulness of the technique.

Epicardial coronary arteries, throughout most of their length, are directly contiguous with various venous structures. For example, the proximal and mid right coronary artery runs in the atrio-ventricular groove between the right atrium and right ventricle and is separated from the right atrial cavity along the anterior portion of the tricuspid annulus by a few millimeters of tissues which will readily transmit ultrasound. The proximal and mid circumflex coronary artery is directly adjacent to the coronary sinus in the posterior portion of the atrioventricular groove between the left atrium and the left ventricle. The coronary sinus is readily accessible to catheters introduced into the right atrium. The coronary sinus in most patients is greater than 4 mm in diameter and is routinely instrumented with catheters during electrophysiologic studies. The great coronary vein runs immediately alongside the mid and distal left anterior descending coronary artery, and can be accessed from the coronary sinus.

Thus the venous system is ideally structured to guide catheters to and along periarterial regions adjacent to epicardial coronary arteries. Another advantage of the venous system is that it is not prone to disease processes, particularly coronary atherosclerosis. Such diseases can restrict the lumen of an arterial vessel so that a catheter can not pass through the diseased portion of the vessel. Thus, with intraarterial ultrasound imaging, it is often impossible to image the diseased portions of the vessel which are of greatest interest to a physician. Portions of the vessel on the far side of any blockage, are of course impossible to image intraarterially. By maneuvering a catheter through the venous system however, an adjacent artery, including blockages and areas beyond blockages, can be imaged.

Finally, compared to arterial structures, venous structures are more readily accessible and do not pose as many access related complications. In most patients, the right atrium and coronary sinus can be safely accessed with much larger diameter catheters than those which can be used for intraarterial ultrasound devices. Other venous structures also generally have a greater diameter than corresponding arterial structures thereby enabling the use of larger catheters.

Thus, venous structures offer several advantages over arterial structures as catheter guides for the imaging of epicardial arteries. An example of a periarterial intravascular imaging procedure is now discussed in relations to FIG. 1, which shows the human heart, with principal arterial and venous structures, in schematic form.

An ultrasound catheter with over-the-guide wire capability is introduced into the venous system through the femoral vein. Alternatively, with small diameter catheters, the external jugular or the antecubital veins can be used for access to the central venous system. The catheter is then advanced to the right atrium 1. Once in the right atrium 1 the catheter can be positioned with its tip in the most superior and anterior segment of the arterial aspect of the tricuspid annulus 3. Ultrasound imaging of the right coronary artery 4 is then begun. The tip of the catheter is then gradually swept more inferiorly along the tricuspid annulus to image more distal parts of the right coronary artery 4. Next the tip of the catheter can be maneuvered into the coronary sinus 2 to image the circumflex coronary artery 5. The catheter can then be maneuvered through the great cardiac vein 6 and its branches for imaging of the left anterior descending coronary artery 7 and its branches.

Other periarterial imaging opportunities will be apparent to those skilled in the art. For example, imaging of the branches of the right and circumflex arteries may be made from the small cardiac vein 8 and the middle cardiac vein 9, respectively.

Figure 2:
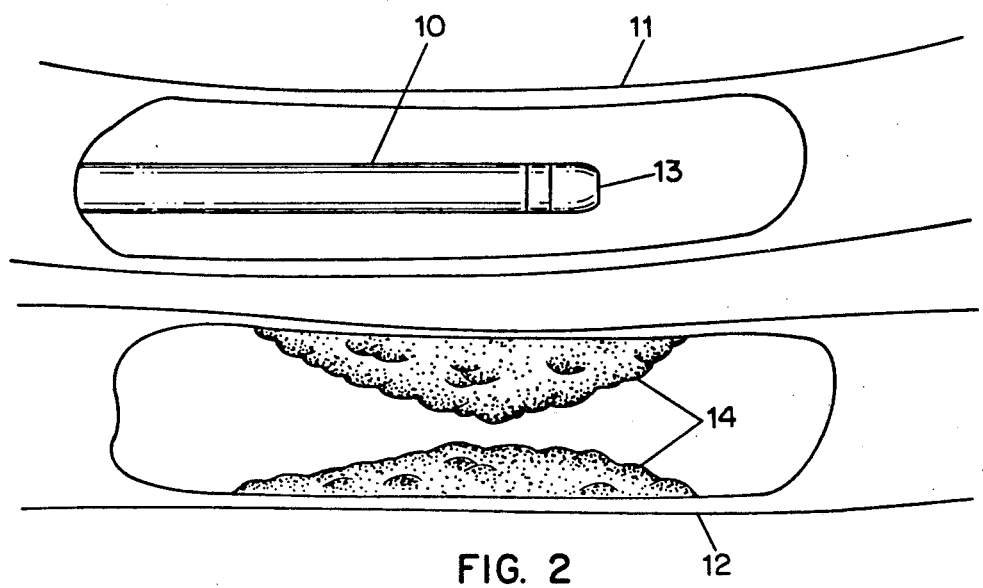
FIG. 2 is a representation of a periarterial ultrasound imaging catheter in a vein adjacent to an artery to be imaged.

FIG. 2 shows, in schematic form, the positioning of a periarterial ultrasound imaging catheter 10 in a vein 11 adjacent to the diseased artery 12. The catheter images a cross-section of the vein and artery which is perpendicular to the axis of the catheter. As can be seen in FIG. 2, the diseased (e.g. atherosclerotic) portion 14 of the artery 12 would prevent an intraarterial imaging catheter from passing through the length of the artery and thus limit the information available to the investigator using the prior art technique.

The periarterial technique also enables longitudinal imaging of the artery 12 to show the length and severity of the blockage 14. In one method, the signals obtained in successive scans taken periarterially along the length of the artery are processed by appropriate programming of the imaging circuitry to develop three-dimensional or longitudinal images of the artery. This, of course, is not possible in intraarterially where the blockage can prevent the passage of an ultrasound catheter. In another method, the tip of the catheter can be maneuvered so that the ultrasound scan sweeps through angle which encompasses a section of artery. A longitudinal image can then be obtained.

The catheter is radiopaque so as to permit viewing under fluoroscopy. At the forward end of the catheter is a soft tip 13 which minimizes the risk of vascular perforation. The transducer is set back from the soft tip. Current ultrasound catheters rotate a beam of ultrasound energy through 360° at a rate of about 1800 R.P.M., either electronically or mechanically (e.g. by means of a rotating mirror). Periarterial catheters, because of their position outside of an artery, do not require a full 360° scan and are controlled accordingly by the scanning means. The imaging system employed in the present invention includes the usual electronic digital processor for developing two- and three-dimensional images from the reflected ultrasonic signals and a display monitor. A drive module would also be required for systems which utilize mechanical scanning.

The design of a catheter based periarterial ultrasound imaging system is generally similar to that of a catheter based intraarterial ultrasound imaging system. One such catheter based ultrasound imaging system used in intraarterial imaging is manufactured by InterTherapy of 1001 W. 17th St., Costa Mesa, Calif. 92627. In contrast to intraarterial ultrasound imaging catheters which operate at a frequency of 20-40 MHz, a periarterial ultrasound imaging catheter preferably should operate at a frequency of 15-20 MHz. This provides for a greater imaging field depth and compensates for the fact that a periarterial catheter must develop images from a greater distance in comparison to intraarterial catheters.

The greater diameter of the venous system allows for a periarterial ultrasound imaging catheter tip diameter of 7-10 French (2.3 mm-3.3 mm). The larger catheter diameter relaxes some of the stringent constraints previously imposed on catheter and transducer design by the small size of the arterial systems. In solid state transducers, for example, it may allow for a larger number of elements in the phase array signal source, which may translate in improved image resolution. Less signal deterioration during transmission from the transducer to the processor can also be expected with larger diameter catheters. A larger tip diameter also allows for catheters which can contain multiple transducers or variable angle transducers. Catheters with a number of transducers along their length can be used to develop three-dimensional and longitudinal images. Variable angle transducers permit the angle of the ultrasound beam to be varied without maneuvering of the catheter tip.

Furthermore, a periarterial ultrasound imaging catheter does not require a delivery sheath. The sheath is required in intraarterial ultrasound systems to prevent snagging of the catheter on atheroma. Surfaces of venous structures, however, are free of atheromatous plaque and a sheath is unnecessary.

The signal processing and imaging producing apparatus is essentially the same as that used in intraarterial ultrasound imaging systems, modified to develop longitudinal images and to handle the lower frequency signals generated by the periarterial ultrasound catheter. Such modifications would be obvious to those skilled in the art.

While a preferred embodiment of the invention has been described, those skilled in the art will recognize that modifications, to what has been specifically described can be made without exceeding the scope of the invention. For instance, imaging means other than ultrasound imaging means can be used in accordance with the periarterial methods described herein. The present invention is intended to be limited only by the scope of the appended claims.

I claim:

1. A periarterial method of imaging a human artery comprising:
   introducing means for imaging into a venous system of a human subject to be imaged;
   guiding said means for imaging through said venous system to points in said venous system adjacent to an artery of said subject;
   imaging said artery with said means for imaging from said adjacent points in said venous system.

2. The method of claim 1 wherein said means for imaging is introduced into said venous system by way of the femoral vein, the external jugular vein or the antecubital veins.

3. The method of claim 1 wherein fluoroscopy is used to guide said means for imaging.

4. The method of claim 1 wherein said means for imaging is swept along the tricuspid annulus of said venous system to image said subject's right coronary artery.

5. The method of claim 1 wherein said means for imaging is maneuvered through the great cardiac vein of said venous system and its branches to image said subject's left anterior descending coronary artery and its branches.

6. The method of claim 1 wherein said means for imaging is maneuvered through the coronary sinus of said venous system to image said subject's circumflex coronary artery.

7. The method of claim 1 wherein said means for imaging comprises an ultrasound imaging catheter.

8. The method according to claim 7 wherein the step of imaging said artery with said means for imaging comprises:
   transmitting ultrasonic energy from said ultrasonic imaging catheter in said venous system, through the walls of said venous system and through said artery, some of said ultrasonic energy being reflected by said artery;
   said ultrasound imaging catheter receiving some of said reflected ultrasound energy; and
   creating visual images of said artery from said received energy.

9. The method according to claim 8 wherein the transmitted ultrasonic energy has a frequency of 15–20 MHz.

* * * * *